United States Patent [19]
Chao et al.

[11] Patent Number: 5,370,740
[45] Date of Patent: Dec. 6, 1994

[54] CHEMICAL DECOMPOSITION BY SONICATION IN LIQUID CARBON DIOXIDE

[75] Inventors: Sidney C. Chao, Manhattan Beach; Edna M. Purer, Los Angeles, both of Calif.

[73] Assignee: Hughes Aircraft Company, Los Angeles, Calif.

[21] Appl. No.: 130,333

[22] Filed: Oct. 1, 1993

[51] Int. Cl.$^5$ .............................. B08B 3/12; C02F 1/36
[52] U.S. Cl. .......................................... 134/1; 134/10; 210/748; 204/157.15
[58] Field of Search ........................... 134/1, 42, 10, 2; 204/158.2, 157.15; 210/748, 759, 760

[56] References Cited

U.S. PATENT DOCUMENTS

| | | | |
|---|---|---|---|
| 4,906,387 | 3/1990 | Pisani | 210/748 |
| 4,990,260 | 2/1991 | Pisani | 210/664 |
| 5,013,366 | 5/1991 | Jackson et al. | 134/1 |
| 5,068,040 | 11/1991 | Jackson | 210/748 |
| 5,213,619 | 5/1993 | Jackson et al. | 134/1 |

Primary Examiner—Paul Lieberman
Assistant Examiner—Lorna M. Douyon
Attorney, Agent, or Firm—M. E. Lachman; M. W. Sales; W. K. Denson-Low

[57] ABSTRACT

Sonication is employed in the destruction of organic chemicals, using liquid carbon dioxide as the sonicating medium. The process of the invention for decomposing at least one chemical comprises: (a) providing a sonicating vessel equipped with an array of sonicators; (b) introducing the chemical to be decomposed into the sonicating vessel, together with liquid carbon dioxide; and (c) exposing the chemical in the sonicating vessel to sonication for a period of time sufficient to cause the chemical to decompose to form at least one decomposition product. The sonication process may additionally employ one or more of ultraviolet light, oxidizing modifiers such as water, sodium hypochlorite, ozone, or hydrogen peroxide, and reaction-quenching species such as hydrogen ($H_2$). Depending on the nature of the decomposition product(s), disposal may range from simple concentration of the product and collection thereof (in the case of liquids or solids), to venting to the atmosphere (in the case of gaseous, inert products), to venting to the atmosphere through an appropriate gas-trap (in the case of gaseous product that are toxic, reactive, or considered to be environmentally-controlled substances).

18 Claims, 2 Drawing Sheets

CHEMICAL DECOMPOSITION BY SONICATION IN LIQUID CARBON DIOXIDE

BACKGROUND OF THE INVENTION

1. Field of the invention

The present invention relates to the chemical decomposition of organic molecules, and, more particularly, to chemical decomposition through the use of sonication in liquid carbon dioxide.

2. Description of Related Art

Ultrasonic cleaning has been utilized by industry for a number of years. In the conventional processes, the sonicating media are organic solvents, or water and aqueous solutions, and ultrasonic energy is applied to the media to promote cavitation, i.e., the formation of "vacuum" bubbles and their subsequent collapse. Although adequate for the sonication cleaning, both of these approaches has a significant disadvantage. The use of organic and aqueous solvents as sonicating media present the problem of chemical disposal of the spent sonication medium and is subject to strict regulatory controls. An additional disadvantage relates to handling of the removed contaminant(s), whether organic or particulate. When the contaminant is a controlled material, once in solution or suspension, its volume is substantially increased, and this presents an additional post-treatment/disposal problem.

In these conventional ultrasonic cleaning processes, sonic horns are often used to produce the sonic energy. In other processes, a cavitation nozzle may be used. For example, U.S. Pat. No. 4,906,387, issued Mar. 6, 1990, to J. Pisani for "Method for Removing Oxidizable Contaminants in Cooling Water Used in Conjunction with a Cooling Tower" and U.S. Pat. No. 4,990,260, issued Feb. 5, 1991, to J. Pisani for "Method and Apparatus for Removing Oxidizable Contaminants in Water to Achieve High Purity Water for Industrial Use" disclose methods for removing contaminants from water by inducing cavitation in the water to cause the water to dissociate to produce hydroxyl free-radicals which act as oxidizing agents. In the processes of Pisani, ultraviolet (UV) radiation is used in combination with cavitation to continue the oxidation process which was initiated by the hydroxyl free-radicals. The cavitation in the Pisani processes is produced by a "critical flow" nozzle.

Another type of cleaning process, utilizing phase shifting of dense phase gases, has been disclosed and claimed in U.S. Pat. No. 5,013,366, issued to D. P. Jackson et al and assigned to the same assignee as the present application. The process employs a dense phase gas at or above the critical pressure. The phase of the dense phase gas is then shifted between the liquid state and the supercritical state by varying the temperature of the dense fluid in a series of steps between temperatures above and below the critical temperature of the dense fluid, while maintaining the pressure above the critical value. Examples of fluids include (1) hydrocarbons, such as methane, ethane, propane, butane, pentans, hexane, ethylene, and propylene; (2) halogenated hydrocarbons, such as tetrafluoromethane, chlorodifluoromethane, and perfluoropropane; (3) inorganics, such as carbon dioxide, ammonia, helium, krypton, argon, sulfur hexafluoride, and nitrous oxide; and (4) mixtures thereof. In alternative embodiments, the dense phase gas may be exposed to UV radiation during the cleaning process or ultrasonic energy may be applied during the cleaning process to agitate the dense phase gas and the substrate surface. These treatments enhance removal efficiency of the contaminant from the surface being cleaned, but still result in a waste stream requiring further treatment and/or disposal.

More recently, in view of environmental concerns about the contaminating effect of certain organic molecules, investigations have begun to determine ways to deal with such organics. In one approach, destruction of organics such as polychlorobenzenes (PCBs) through irradiation with 20 Kilohertz (Khz) sonic energy has been recently documented, using nonaqueous solvents as extracting/sonicating medium. Ultrasonic energy has also been used in conjunction with hydrogen peroxide to treat gasoline/benzene contaminated ground water. During cavitation, the energy of the imploding bubbles initiate the decomposition reactions.

The use of solvents (aqueous or organic) as sonicating media presents the problem of the sonicating media disposal/regeneration and the disposal of the reaction products themselves. Accordingly, there is a need to provide a method of destroying organic molecules, employing a sonicating medium that presents no environmental disposal problems.

SUMMARY OF THE INVENTION

In accordance with the invention, sonication is employed in the destruction of organic chemicals, using liquid carbon dioxide as the sonicating medium. The destruction of the organic chemicals is accomplished with the intense vibrations and the cavitation produced by the passage of sound through the liquid sonicating medium, with, or without the aid of ultraviolet light, or modifiers such as water, sodium hypochlorite, ozone, or hydrogen peroxide, and reaction quenching species such as, but not limited to, hydrogen ($H_2$).

The process of the invention for decomposing at least one chemical comprises (a) providing a sonicating vessel equipped with an array of sonicators;

(b) introducing the chemical to be decomposed into the sonicating vessel, together with liquid carbon dioxide;

(c) exposing the chemical in the sonicating vessel to sonication for a period of time sufficient to cause the chemical to decompose to form at least one decomposition product.

Depending on the nature of the decomposition product(s), disposal may range from simple concentration of the product and collection thereof (in the case of liquids or solids), to venting to the atmosphere (in the case of gaseous, inert products), to venting to the atmosphere through an appropriate gas-trap (in the case of gaseous product that are toxic, reactive, or considered to be environmentally-controlled substances).

The process of the invention thus provides a facile way of decomposing undesired chemicals and disposing of the decomposition products.

DESCRIPTION OF THE PREFERRED EMBODIMENTS

Carbon dioxide is a readily available, inexpensive, nontoxic and easily liquefiable natural resource, at relatively low pressures and mild temperatures. In a closed loop, recirculating, liquid $CO_2$ regenerating system, the decomposition products can be readily separated from the sonicating medium. The separation can be accomplished either by decompression, filtration (chemical or physical), or a combination of both. Through the decompression of the liquid $CO_2$, the condensible decomposition products drop out in a concentrated form that allows for waste disposal or recovery. The fluid is then regenerated by recompression.

The use of $CO_2$ as a sonicating medium thus provides the potential of an environmentally safe way to deal with decomposition products resulting from the sonication. There are several different ways in which the resulting decomposition products can be separated from the $CO_2$ medium. This separation is a function of the nature of the decomposition product: liquid, solid, or gaseous. Five such exemplary ways of separation, along with the $CO_2$ reclamation and the associated process flow charts are discussed below. The apparatus that may be suitably employed in the practice of each process is discussed with reference to FIG. 1, and, in some cases, with reference to FIG. 2.

Figure 1:
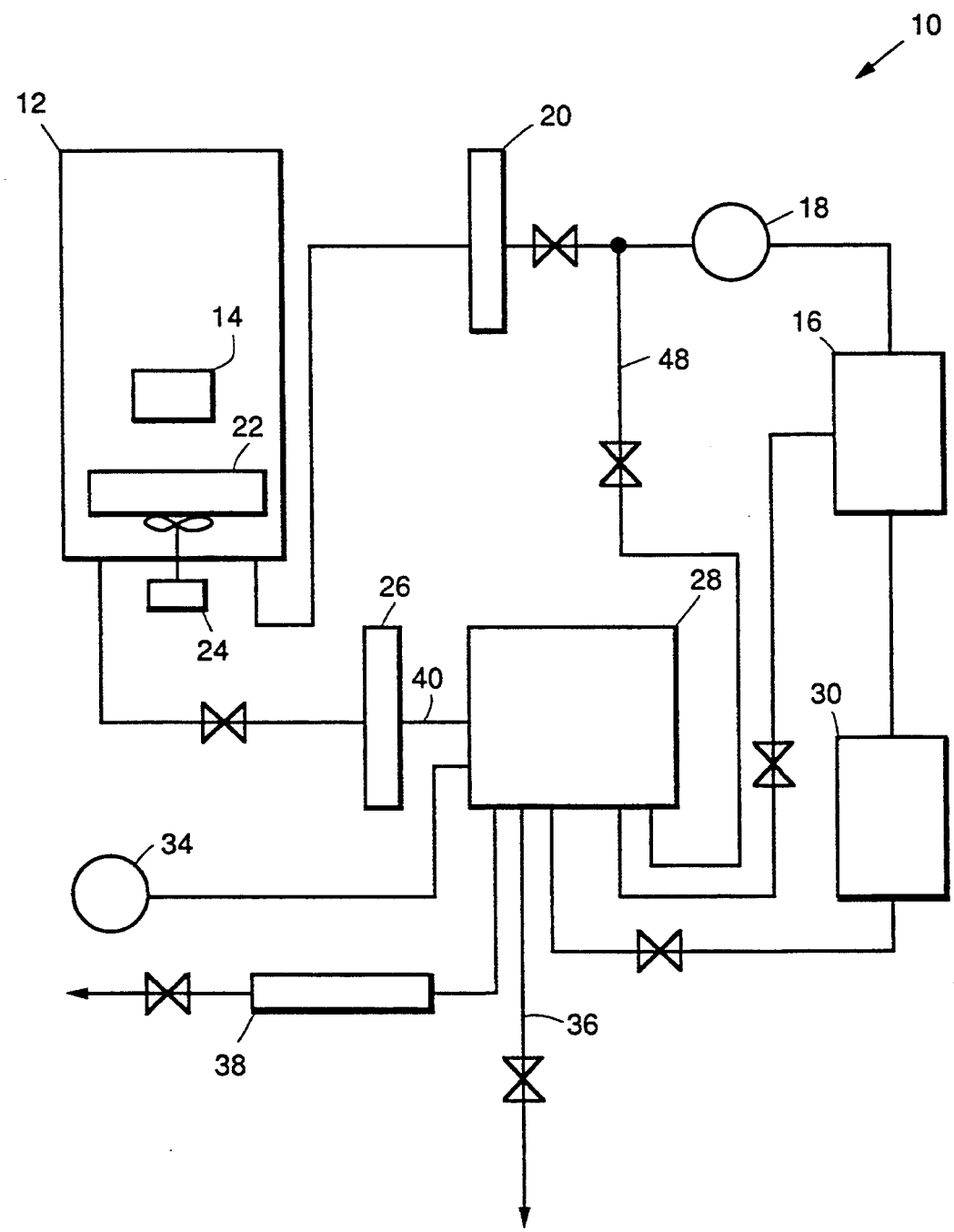
FIG. 1 is a schematic diagram of an exemplary cleaning system useful in practicing the method of the invention.

FIG. 1 depicts an example of a self-contained, automated, computer controlled, $CO_2$ recirculating and regenerating dense phase fluid/liquid cleaning system 10, such as the SUPERSCRUB ™ precision cleaning equipment (a trademark of Hughes Aircraft Company).

Figure 2:
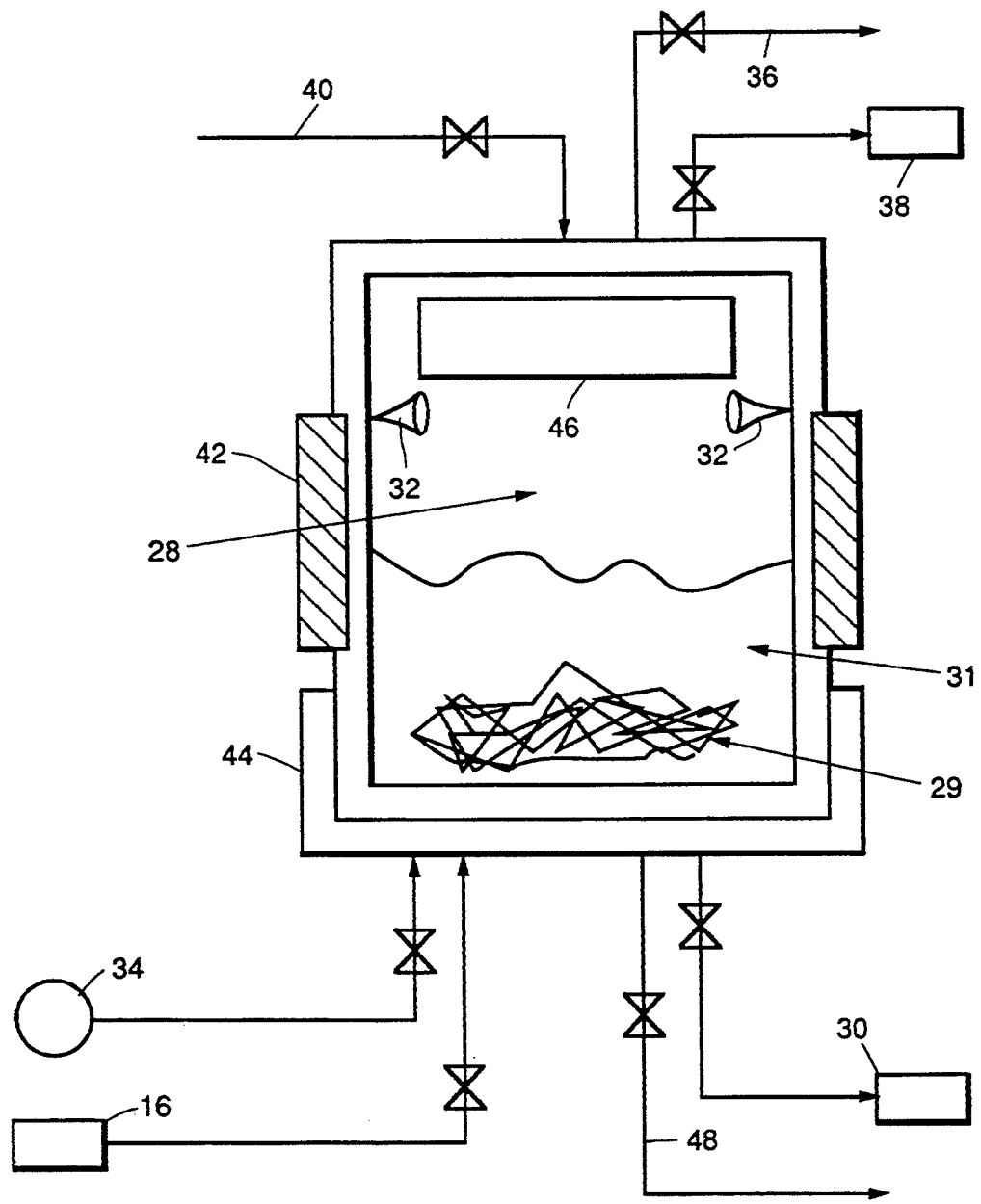
FIG. 2 is a schematic diagram of an exemplary separator/sonicating reaction chamber used in the cleaning system shown in FIG. 1.

FIG. 2 shows an exemplary separator/sonicating vessel 28, useful in the system 10 depicted in FIG. 1, incorporating a sonic horn, or array of horns, or transducers, and generator. The sonicators (horn/array of horns, transducers/transducer arrays), as well as the generator power and operational frequencies (20 Khz and above) are application-dependent.

In the first phase of the process, substrates 14 to be cleaned are loaded in the cleaning vessel 12. Liquid $CO_2$ is pumped into the cleaning vessel 12 from storage vessel 16 by a cryogenic pump 18, after gasification in preheater 20. The cleaning vessel 12 is then further pressurized and heated to preset supercritical process pressures and temperatures, when flow through is started for a predetermined time. The pressure is maintained above 1,100 psi (77.3 Kg/cm$^2$) and the temperature is maintained above 31° C. The targeted organic contamination is solvated and removed with the effluent supercritical $CO_2$.

Other aspects of the cleaning vessel 12 include a heater 22 within the vessel to control temperature and a mixer or stirrer 24 to ensure appropriate agitation of the supercritical carbon dioxide. Following discharge from the cleaning vessel 12, the effluent carbon dioxide is either heated with a preheater 26 to gasify it and then introduced into the separator/sonicating vessel 28, or introduced directly into the separator/sonicating vessel 28, which is provided with heating means described below.

The effluent is decompressed into the heated separator/sonicating vessel 28, or through the preheater 26, where the contamination 29 drops out in a concentrated form. The now gaseous $CO_2$ is reliquefied in a condenser 30 and returned to the $CO_2$ storage tank 16.

In the second phase, following the completion of the cleaning/extraction process, liquid $CO_2$ 31 is pumped from the liquid storage vessel 16 into the separator/sonicating vessel 28 up to a predetermined pressure/temperature. Sonication is started with an array of transducers or horns 32 for a predetermined period of time. The position of the sonicating horns within the separator/sonicating vessel 28 may be at any location, including the top, bottom, sides, and any combination thereof.

The sonication step to decompose the organic molecules is carried out at a temperature below 32° C., in order to ensure that the carbon dioxide is in liquid form. The pressure may vary as necessary, so long as the carbon dioxide is maintained in the liquid state.

Sonication is carried out at a frequency within the range of about 5 to 100 Kilohertz. However, commercial ultrasonic generators typically operate at a frequency of about 20 to 90 Kilohertz, and these generators are advantageously employed in the practice of the present invention.

An oxidizing modifier may be added to the liquid carbon doixide in order to provide an activating medium. Such a modifier, being more thermodynamically reactive than $CO_2$, can serve to accelerate the chemical decomposition reaction. $CO_2$ then serves as the fluid medium in which the oxidation process is conducted. Examples of modifiers suitably employed in the practice of the invention include water, sodium hypochlorite, ozone, and hydrogen peroxide. The amount of modifier, if added, is less than about 25 weight percent (wt %) of the total medium. More than about 25 wt % is not required, due to the reaction acceleration provided by the supercritical medium. Oxidizing modifiers are delivered to the separator/sonicating vessel 28 via a modifier pump 34 from a reservoir (not shown).

Ultraviolet (UV) radiation (not shown) may also be used to accelerate the chemical decomposition process. The range of UV radiation used is from about 180 to 300 nanometers. The UV radiation may be used alone or in conjunction with the oxidizing modifier.

A reaction-quenching species may be added in order to regulate this highly reactive environment. An example of such a reaction-quenching species is hydrogen, although the invention is not limited to hydrogen as the reaction-quenching species. The amount of the reaction-quenching species, if added, is about 0.1 to 1.0 wt %. The amount added is a function of the extent to which quenching is required.

At the completion of the sonication step, the liquid $CO_2$ sonicating media is reclaimed and the decomposition products are removed for disposal.

The mechanism of decomposition-product/$CO_2$ media separation, and $CO_2$ medium reclamation, is a function of the nature of the decomposition products. Five different methods of dealing with this are now described.

(A) Decomposition product is liquid or solid, but soluble/partially soluble in liquid $CO_2$.

After the sonic treatment, the liquid $CO_2$ is gasified, maintaining subcritical conditions. The gaseous $CO_2$ is de-compressed directly to the condenser 30, where it is reliquefied and returned to storage 16. The separator 28 is then opened and the concentrated decomposition products removed for disposal. The exemplary process flow chart of this embodiment is shown below.

| Reaction Products Are Soluble/Partially Soluble in Liquid $CO_2$ |
|---|
| PURGE → <br> → PRESSURE/TEMPERATURE ADJUSTMENT SUPERCRITICAL PHASE → <br>　the targeted chemical is solvated/extracted at <br>　this stage by the supercritical $CO_2$ <br> → FLOW THROUGH AND EFFLUENT DECOMPRESSION INTO THE SEPARATOR → <br>　the targeted chemical is dropped out of the gasified $CO_2$ stream into the separator <br> → LIQUID $CO_2$ IS PUMPED INTO THE SEPARATOR AND THE MIXTURE IS SONICATED → <br>　sonic treatment breaks down the targeted chemical <br> → THE SEPARATOR IS DECOMPRESSED INTO THE CONDENSER → <br>　liquid/solid decomposition products drop out <br> → DECOMPOSITION PRODUCTS ARE REMOVED FROM SEPARATOR |

(B) Decomposition product is solid, but insoluble in liquid $CO_2$.

The separator 28 is retrofitted with an appropriate filtration system, the liquid $CO_2$ reclaimed through a filtration step without gasification, and then returned directly to storage 16. The separator 28 is then opened and the concentrated decomposition products removed for disposal. The exemplary process flow chart of this embodiment is shown below.

| Reaction Products Are Solid and Insoluble in Liquid $CO_2$ |
|---|
| PURGE → <br> → PRESSURE/TEMPERATURE ADJUSTMENT TO SUPERCRITICAL PHASE → <br>　the targeted chemical is solvated/extracted at <br>　this stage by the supercritical $CO_2$. <br> → FLOW THROUGH AND EFFLUENT DECOMPRESSION INTO THE SEPARATOR → <br>　the targeted chemical is dropped out of the gasified $CO_2$ stream into the separator <br> → LIQUID $CO_2$ IS PUMPED INTO THE SEPARATOR AND THE MIXTURE IS SONICATED → <br>　sonic treatment breaks down the targeted chemical <br> → LIQUID $CO_2$ FILTERED OUT OF THE SEPARATOR BACK TO STORAGE → <br> → FINAL VENTING OF SEPARATOR TO ATMOSPHERE AND DECOMPOSITION PRODUCT REMOVAL |

(C) Decomposition product is gaseous, but inert, and is vented directly to the atmosphere.

The decomposition product is directly vented to the atmosphere along line 36. The exemplary process flow chart of this embodiment is shown below.

| Reaction Products Are Gaseous and Inert |
|---|
| PURGE → <br> → PRESSURE/TEMPERATURE ADJUSTMENT TO SUPERCRITICAL PHASE → <br>　the targeted chemical is solvated/extracted at <br>　this stage by the supercritical $CO_2$ <br> → FLOW THROUGH AND EFFLUENT DECOMPRESSION INTO THE SEPARATOR → <br>　the targeted chemical is dropped out of the gasified $CO_2$ stream into the separator <br> → LIQUID $CO_2$ IS PUMPED INTO THE SEPARATOR AND THE MIXTLTRE IS SONICATED → <br>　sonic treatment breaks down the targeted chemical <br> → VENT TO ATMOSPHERE |

(D) Decomposition product is gaseous, but toxic, reactive or controlled.

In this case, the decomposition product is decompressed to the atmosphere through an appropriate gastrap 38. The exemplary process flow chart of this embodiment is shown below.

| Reaction Products Are Gaseous But Toxic, Or Reactive |
|---|
| PURGE → <br> → PRESSURE/TEMPERATURE ADJUSTMENT TO SUPERCRITICAL PHASE → <br>　the targeted chemical is solvated/extracted at <br>　this stage by the supercritical $CO_2$ <br> → FLOW THROUGH AND EFFLUENT DECOMPRESSION INTO THE SEPARATOR → |

| Reaction Products Are Gaseous But Toxic, Or Reactive |
|---|
| the targeted chemical is dropped out of the gasified $CO_2$ stream into the separator<br>→ LIQUID $CO_2$ IS PUMPED INTO THE SEPARATOR AND THE MIXTURE IS SONICATED →<br>   sonic treatment breaks down the targeted chemical<br>→ DECOMPRESS TO ATMOSPHERE THROUGH AN APPROPRIATE GAS-TRAP |

In another embodiment of this invention, when the chemical to be decomposed is a process by-product, the supercritical cleaning step is omitted and the process is simplified to the flow illustrated below. The $CO_2$ and entrained contaminant(s) are introduced along line 40, which is the same line used to introduce the effluent carbon dioxide from the cleaning vessel 12 if the supercritical cleaning step is employed.

| Process By-Product Sonic Decomposition |
|---|
| PURGE →<br>→ LIQUID $CO_2$ IS PUMPED INTO THE SONICATING VESSEL AND THE MIXTURE IS SONICATED →<br>   sonic treatment breaks down the targeted chemical<br>→ CHAMBER IS DECOMPRESSED PER ONE OF THE PREVIOUSLY REFERENCED SCHEDULES, DEPENDING ON THE NATURE OF THE DECOMPOSITION PRODUCTS |

The separator/sonicator 28 is additionally provided with a heater 42 and a cooling jacket 44 for controlling the temperature of the carbon dioxide therein. A filter/demister 46 is also employed to enhance the removal of aerosolized or particulate contaminants in the effluent stream. Line 48 permits introduction of liquid $CO_2$ to the separator/-sonicating vessel 28 from the liquid storage vessel 16 through the cryogenic pump 18.

Thus, there has been disclosed a process for the chemical decomposition of organic chemicals by sonication in liquid carbon dioxide. It will be appreciated by those skilled in the art that various modifications and changes of an obvious nature may be made without departing from the scope of the invention, and all such modifications and changes are intended to fall within the scope of the invention, as defined by the appended claims.

What is claimed is:

1. A process for decomposing at least one organic contaminant, consisting of the steps of:
   (a) removing said at least one organic contaminant from a chosen substrate by supercritical cleaning by
      (1) placing said substrate in a cleaning vessel,
      (2) introducing into said cleaning vessel liquefied carbon dioxide formed by applying at least one of a pressure of at least 1,100 pounds per square inch (77.3 Kg/cm$^2$) and a temperature of at least about 31° C. to gaseous carbon dioxide and contacting said substrate containing said at least one organic contaminant with said liquefied carbon dioxide to extract said at least one organic contaminant from said substrate, and
      (3) removing said liquefield carbon dioxide and said at least one organic contaminant from said cleaning vessel; an
   (b) decomposing said at least one organic contaminant by
      (1) providing a sonicating vessel equipped with an array of sonicators,
      (2) introducing said at least one organic contaminant into said sonicating vessel, together with liquid carbon dioxide and, optionally, a substance selected from the group consisting of at least one oxidizing modifier and at least one reaction-quencher species, and
      (3) exposing said at least one organic contaminant in said sonicating vessel to said sonication means for a period of time sufficient to cause said at least one organic contaminant to decompose to form at least one decomposition product.

2. The process of claim 1 wherein said liquid carbon dioxide is maintained at a temperature of less than 32° C.

3. The process of claim 1 wherein said at least one oxidizing modifier is selected from the group consisting of water, sodium hypochlorite, ozone, and hydrogen peroxide.

4. The process of claim 3 wherein said oxidizing modifier is added in an amount up to about 25 weight percent.

5. The process of claim 1 wherein said at least one reaction-quencher species is added to said liquid carbon dioxide during the formation of said at least one decomposition product.

6. The process of claim 5 wherein said reaction-quencher species consists essentially of hydrogen.

7. The process of claim 6 wherein said reaction-quencher is added in an amount of about 0.1 to 1.0 weight percent.

8. The process of claim 1 wherein said sonication is carried out at a frequency ranging from about 5 to 100 Kilohertz.

9. The process of claim 8 wherein said sonication is carried out at a frequency ranging from about 20 to 90 Kilohertz.

10. The process of claim 1 wherein said at least one decomposition product is liquid or solid and is partially or totally soluble in liquid carbon dioxide.

11. The process of claim 10 wherein after said sonication, said liquid carbon dioxide is gasified, maintaining subcritical conditions, to thereby concentrate said at least one decomposition product, and the gasified carbon dioxide is decompressed directly to a condenser for reliquefaction and returned to a storage reservoir, while said sonicating vessel is opened and said at least one decomposition product is removed for disposal.

12. The process of claim 1 wherein said at least one decomposition product is solid and insoluble in liquid carbon dioxide.

13. The process of claim 12 wherein after sonication said liquid carbon dioxide is passed through a filter to thereby concentrate said at least one decomposition product and is then returned to a storage reservoir, while said sonicating vessel is opened and said at least one decomposition product is removed for disposal.

14. The process of claim 1 wherein said at least one decomposition product is gaseous and inert.

15. The process of claim 14 wherein said at least one decomposition product is vented to the atmosphere.

16. The process of claim 1 wherein said at least one decomposition product is gaseous and is at least one of toxic, reactive, or an environmentally controlled substance.

17. The process of claim 16 wherein said at least one decomposition product is vented to the atmosphere through an appropriate gas-trap for treatment.

18. The process of claim 1 wherein said liquefied carbon dioxide is gasified so as to concentrate said at least one chemical in said sonicating vessel, said gasified liquid carbon dioxide is removed from said sonicating vessel, and liquid carbon dioxide is introduced into said sonicating vessel, prior to exposing said chemical to said sonication means.

* * * * *